US012636049B2

(12) United States Patent
Bigdeli-Issazadeh

(10) Patent No.: US 12,636,049 B2
(45) Date of Patent: May 26, 2026

(54) INTERMEDIATE FEMORAL NAIL

(71) Applicant: Stryker European Operations Limited, Carrigtwohill (IE)

(72) Inventor: Sabine Bigdeli-Issazadeh, Felde (DE)

(73) Assignee: Stryker European Operations Limited, Carrigtwohill (IE)

( * ) Notice: Subject to any disclaimer, the term of this patent is extended or adjusted under 35 U.S.C. 154(b) by 90 days.

(21) Appl. No.: 18/387,290

(22) Filed: Nov. 6, 2023

(65) Prior Publication Data

US 2024/0148417 A1 May 9, 2024

Related U.S. Application Data

(60) Provisional application No. 63/423,187, filed on Nov. 7, 2022.

(51) Int. Cl.
*A61B 17/72* (2006.01)
(52) U.S. Cl.
CPC ................................. *A61B 17/7233* (2013.01)
(58) Field of Classification Search
CPC ..... A61B 17/17; A61B 17/1725; A61B 17/72; A61B 17/7233; A61B 17/7241; A61B 17/74; A61B 17/744; A61B 17/88; A61B 17/8872
See application file for complete search history.

(56) References Cited

U.S. PATENT DOCUMENTS

| | | | |
|---|---|---|---|
| 3,709,218 A | 1/1973 | Halloran | |
| 4,133,507 A | 1/1979 | Chervenak | |
| 4,135,507 A | 1/1979 | Harris | |
| 4,475,545 A | 10/1984 | Ender | |
| 4,919,673 A | 4/1990 | Willert et al. | |
| 5,041,115 A | 8/1991 | Frigg et al. | |
| 5,066,296 A | 11/1991 | Chapman et al. | |

(Continued)

FOREIGN PATENT DOCUMENTS

| | | |
|---|---|---|
| AU | 2014338523 A1 | 6/2016 |
| EP | 0257118 A1 | 3/1988 |

(Continued)

OTHER PUBLICATIONS

Extended European Search Report issued in Appln. No. 23208201.6 dated Jan. 23, 2024 (8 pages).

(Continued)

*Primary Examiner* — Christopher J Beccia
(74) *Attorney, Agent, or Firm* — Lerner David LLP

(57) ABSTRACT

A femoral nail includes a proximal portion configured to engage a driving tool for driving the femoral nail into a femur, a distal portion remote from the proximal portion, and an intermediate portion extending from and between the proximal portion and distal portion. The intermediate portion has a circular screw hole and an elongated screw hole extending therethrough. The circular screw hole having a central axis, and the elongated screw hole having a first axis and a second axis that are separated by a distance. The central axis of the circular screw hole is located a distance from a proximal end of the femoral nail that is 61-64% of a total length of the femoral nail, and the first axis of the elongated screw hole is located a distance from the proximal end of the femoral nail that is 70-73% of the total length of the femoral nail.

20 Claims, 7 Drawing Sheets

(56)                   References Cited

U.S. PATENT DOCUMENTS

| | | | |
|---|---|---|---|
| 5,176,681 | A | 1/1993 | Lawes et al. |
| 5,454,813 | A | 10/1995 | Lawes |
| 6,010,505 | A | 1/2000 | Asche et al. |
| 6,010,506 | A | 1/2000 | Gosney et al. |
| 6,039,739 | A | 3/2000 | Simon |
| 6,120,504 | A | 9/2000 | Brumback et al. |
| 6,210,414 | B1 | 4/2001 | Lin et al. |
| 6,461,360 | B1 | 10/2002 | Adam |
| 6,702,816 | B2 | 3/2004 | Buhler |
| 6,855,146 | B2 | 2/2005 | Frigg et al. |
| 7,670,340 | B2 | 3/2010 | Brivio et al. |
| 7,947,043 | B2 | 5/2011 | Mutchler |
| 8,317,788 | B2 | 11/2012 | Kaup |
| 8,790,343 | B2 | 7/2014 | McClellan et al. |
| 8,906,024 | B2 | 12/2014 | Schlienger et al. |
| 11,013,540 | B2 | 5/2021 | Petersik et al. |
| 11,253,298 | B2 | 2/2022 | Prien et al. |
| 11,730,525 | B2 | 8/2023 | Petersik et al. |
| 2002/0099379 | A1 | 7/2002 | Adam |
| 2002/0183750 | A1 | 12/2002 | Buhler |
| 2007/0123873 | A1 | 5/2007 | Czartoski et al. |
| 2007/0123874 | A1 | 5/2007 | Czartoski et al. |
| 2008/0009869 | A1 | 1/2008 | Schlienger et al. |
| 2011/0282347 | A1 | 11/2011 | Gordon et al. |
| 2012/0163683 | A1 | 6/2012 | Wilson et al. |
| 2016/0256202 | A1* | 9/2016 | Halder ................. A61B 17/725 |
| 2019/0314065 | A1* | 10/2019 | Petersik .............. A61B 17/921 |

FOREIGN PATENT DOCUMENTS

| | | |
|---|---|---|
| JP | 2012130724 A | 7/2012 |
| JP | 2012-531995 A | 12/2012 |
| RU | 2271768 C1 | 3/2006 |
| WO | 0071040 A1 | 11/2000 |
| WO | 2011002903 A2 | 1/2011 |
| WO | 2013090859 A1 | 6/2013 |
| WO | 2021/176272 A1 | 9/2021 |
| WO | 2021/176274 A1 | 9/2021 |
| WO | 2022049416 A1 | 3/2022 |

OTHER PUBLICATIONS

Extended European Search Report including the Written Opinion for Application No. EP 19168725.0 dated Sep. 3, 2019, 8 pages.
Stryker, "Gamma3® Hip Fracture Nailing System Operative technique", Stryker Trauma GmbH (2022). 68 pgs.

\* cited by examiner

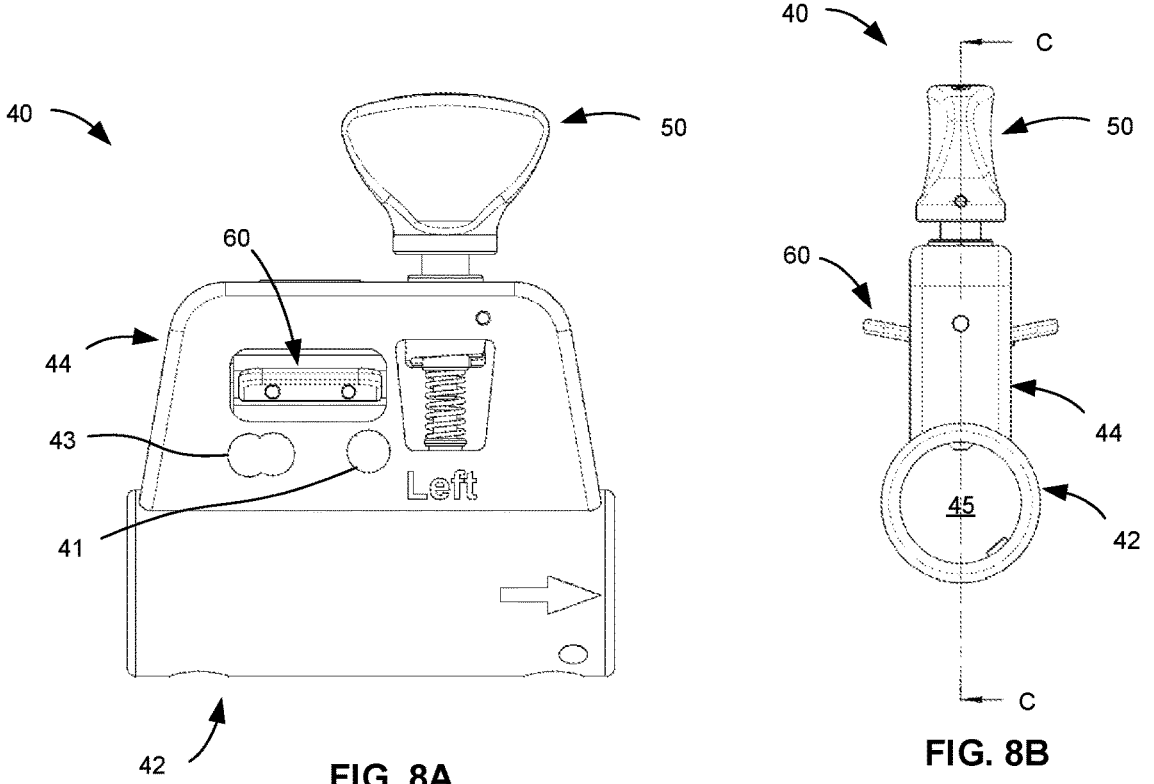
FIG. 8A
FIG. 8B
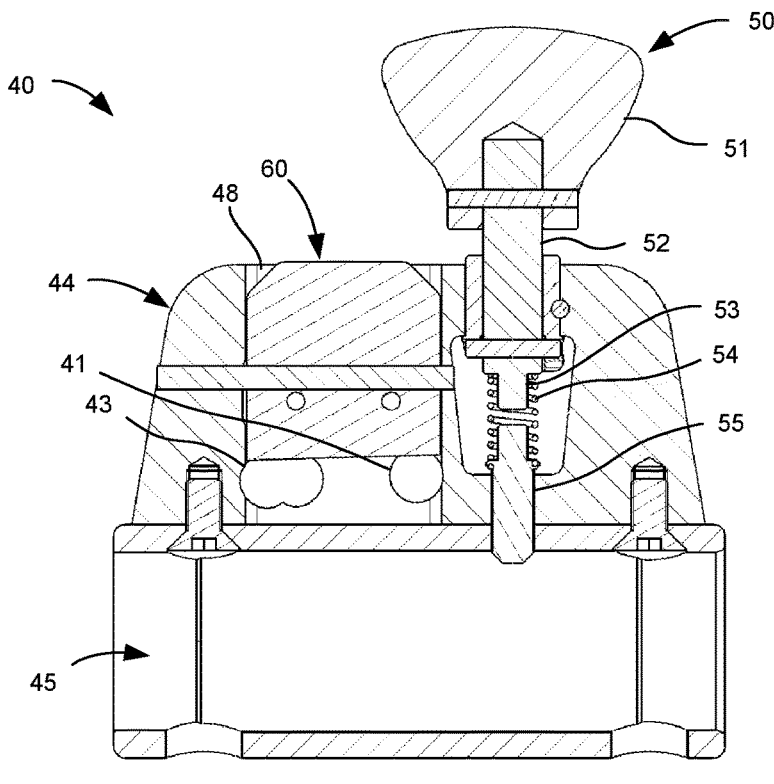
FIG. 8C

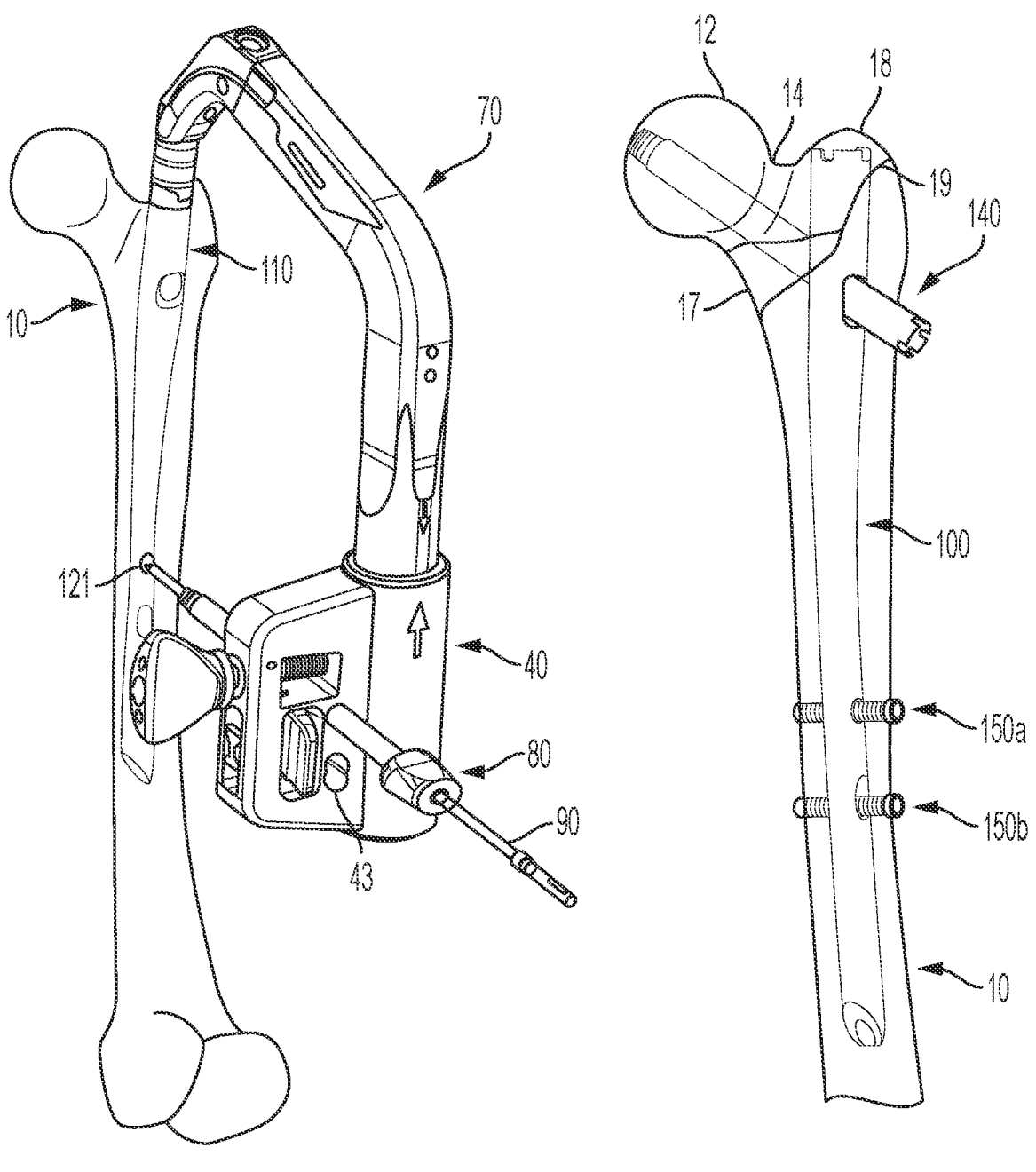
FIG. 9A                    FIG. 9B

FIG. 9C                                        FIG. 9D

INTERMEDIATE FEMORAL NAIL

CROSS REFERENCE TO RELATED APPLICATIONS

The present application claims the benefit of the filing date of U.S. Provisional Patent Application No. 63/423,187 filed Nov. 7, 2022, the disclosure of which is hereby incorporated herein by reference.

BACKGROUND OF THE INVENTION

The skeletal system includes several long bones including the femur. The femur is the longest of the long bones and is generally divided into three regions: the proximal femur, the distal femur, and the femoral shaft. Femoral fractures, which are commonly caused by acute trauma, can occur at or between any one of these regions. The repair of such fractures often involves the use of a femoral, intramedullary nail which is inserted into the intramedullary canal of the femur in an antegrade manner (i.e., through the proximal femur) or in a retrograde manner (i.e., through the distal femur). Such nails are often secured to the bone via a series of bone fasteners which also has the effect of reducing and securing the fractured bone so that healing can occur while allowing the patient to bear weight on the injured limb.

Fractures occurring in the proximal femur, particularly trochanteric, intertrochanteric, subtrochanteric and intracapsular fractures, are typically treated with a short or long intramedullary nail introduced in an antegrade manner. FIG. 1 is a cross-sectional representation of a proximal femur. Short nails, such as nail 20 of FIG. 2A, typically reside within the intramedullary canal of the proximal femur and do not commonly breach the isthmus of the canal which could bend the nail making distal screw targeting more difficult. On the other hand, long nails, such as nail 30 of FIG. 2B, typically extend through the femoral isthmus and may even extend into the diaphysis or metaphysis of the distal femur. In this regard, short nails often involve a less technically demanding procedure, shorter operative time, and less blood loss than long nails. However, long nails compared to short nails are generally more robust and have a lower risk of post-operative periprosthetic fracture.

The geometries of typical short and long nails are also not optimal for the general patient population. Short femoral nails typically have a straight geometry over a majority of their respective lengths which helps facilitate a simpler and faster implantation. This is illustrated in FIG. 2A in which short nail 20 is generally straight and aligned with the short-nail-axis ("SNA"). However, such short nails, because of their straight geometries, do not conform to a typical patient's anatomy which can result in undesirable load distributions that can lead to periprosthetic fractures. Conversely, while long nails are typically more conformal to a natural femur's non-linear geometries, such long nails often impinge on the anterior femoral cortex due to inadequate assumptions and understanding about population level geometric features of femurs potentially resulting in patient discomfort and difficulties with implantation. This has been confirmed by recent database analyses of femurs that have found that certain curvatures of the human femur are greater than originally considered.

Moreover, as previously mentioned, long nails, at least because they breach the isthmus, are typically more difficult and time consuming to implant and secure. This is illustrated by a comparison between short nail 20 and long nail 30. As show, locking screw holes 31 and 33 of long nail 30 are positioned along a distal portion 36 at a distal end of nail 30. Such distal portion 34 extends from a curved intermediate section 34 which itself extends from a straight proximal section 32. In a typical procedure, this distal portion is typically extended into the femoral isthmus which has a tendency to bend distal portion 36 relative to portions 32 and 34. Thus, distal targeting for screw insertion into holes 31 and 32 of long nail 30 is commonly more difficult than for holes 21 and 23 of short nail 20 since the distal end of short nail 20 remains aligned with the SNA after insertion into the femoral canal as it will not breach the isthmus. As such, distal screw targeting for long nail 30 is often performed with the aid of a fluoroscope, which exposes the patient to radiation, and may require multiple adjustments of a targeting instrument to appropriately orient the instrument in alignment with screw holes 31 and 33 resulting in a longer surgical procedure.

While it may be desirable to develop customized nails specific to each patient's own unique geometries to help address some of the above-mentioned problems, this is generally impracticable, at least for the time being. Therefore, there is a need for a femoral nail that is universally adapted to the majority of a patient population and has advantages found with both short and long nails.

BRIEF SUMMARY OF THE INVENTION

The present disclosure describes examples of intermediate length nails which are configured with a universal length. Such universal length has been optimized so that it is as long as possible without breaching the isthmus in order to provide adequate support for the majority of a patient population, such as a first, second, or third standard deviation of a designated patient population. Moreover, such exemplary nails each have curvatures optimized to conform to a population level of femurs with a straight section that includes screw holes optimally located to facilitate ease of implantation and screw targeting. In this regard, such intermediate nails provide the ease of implantation with shorter recovery times commonly found in short nails while obtaining a more robust, conformal fixation commonly found in long nails.

In one aspect of the present disclosure, a femoral nail includes a proximal portion configured to engage a driving tool for driving the femoral nail into a femur, a distal portion remote from the proximal portion, and an intermediate portion extending from and between the proximal portion and distal portion. The intermediate portion has first and second curved segments and first and second straight segments. The first curved segment defines a proximal extent of the intermediate portion, and the second straight segment defines a distal extent of the intermediate portion. The second curved segment is disposed between the first and second straight segments and has a radius of curvature in a first plane. The straight segment having a screw hole extending therethrough.

Additionally, the proximal portion may be straight along its entire length. The distal portion may be angled relative to the second straight segment of the intermediate portion by an angle $\Theta$. The angle $\Theta$ may be about 2 to about 3 degrees. The distal portion may include a distal curved segment and a distal straight segment. The femoral nail may have a total length of 240 mm.

Continuing with this aspect, the distal portion may include a distal curved segment and a distal straight segment. The distal curved segment may interface with the second straight segment of the intermediate portion and may extend distally therefrom. The distal straight segment may extend from the distal curved segment to a distal tip of the femoral nail. The distal portion may interface with the second straight segment of the intermediate portion and may extend distally therefrom to a distal tip of the femoral nail. The distal portion may be curved along its entire length. The first curved segment of the intermediate portion may be curved in a first, second, and third planes. The second curved segment may be curved in the first plane and only in the first plane. The distal portion may be curved along at least a portion of its length and is curved in the first plane. The femoral nail may be cannulated throughout its entire length. The proximal portion may include a transverse bore hole configured to receive a lag screw for insertion into a femoral neck of a femur.

In another aspect of the present disclosure, a femoral nail includes a proximal portion configured to engage a driving tool for driving the femoral nail into a femur and may define a proximal end of the femoral nail. A distal portion remote from the proximal portion and defines a distal end of the femoral nail. An intermediate portion extends from and between the proximal portion and distal portion. The intermediate portion has a curved segment and a straight segment that extends from the curved segment. The straight segment has a proximal extent, a distal extent, and at least one screw hole extending therethrough. The proximal extent and distal extent of the straight segment is respectively about 57-60% and 80-83% of a total length of the femoral nail from the proximal end thereof.

Additionally, the total length may be 240 mm. The proximal portion may be straight along its entire length. The distal portion may be angled relative to the straight segment of the intermediate portion by an angle $\Theta$. The angle $\Theta$ may be about 2 to about 3 degrees. A proximal extent of the curved segment may be about 38-41% of the total length of the femoral nail from the proximal end of thereof, and the distal extent of the curved segment may be the proximal extent of the straight segment. The curved segment may be curved in an anteroposterior plane.

In a further aspect of the present disclosure, a method of repairing a proximal femoral fracture, includes inserting a femoral nail into an intramedullary canal of a femur from a proximal end thereof such that a distal end of the femoral nail is positioned proximal of a femoral isthmus of the femur. The femoral nail has a proximal portion, a distal portion, and an intermediate portion. The proximal portion has a transverse bore hole. The intermediate portion has first and second curved segments and first and second straight segments. The first curved segment defines a proximal extent of the intermediate portion, and the second straight segment defines a distal extent of the intermediate portion. The second curved segment is disposed between the first and second straight segments and has a radius of curvature in a first plane. The straight segment has a static screw hole and a dynamic screw hole extending therethrough. The method also includes inserting a lag screw through the transverse bore hole across at least one fracture line in the proximal femur such that a distal end of the lag screw is disposed at least partially within a femoral head of the femur and inserting a bone screw through the dynamic screw hole and into the bone.

Additionally, the dynamic screw hole may be a longitudinal screw hole that has a proximal end and a distal end. The proximal end may define a first axis, and the distal end may define a second axis. Also, the step of inserting the bone screw through the dynamic screw hole may include inserting the bone screw through the proximal end of the dynamic screw hole. The method may also include inserting another bone screw through the static screw hole and into the bone. The center axis of the static screw hole may be located a distance from a proximal end of the femoral nail 61-64% of a total length of the femoral nail, and the first axis of the dynamic screw hole may be located a distance from the proximal end of the femoral nail 70-73% of the total length of the femoral nail. The total length of the femoral nail may be 240 mm.

Further, the step of inserting the bone screw through the dynamic screw hole may include inserting the bone screw through the distal end of the dynamic screw hole. Also, the method may include comprising inserting another bone screw through the static screw hole and into the bone. A center axis of the static screw hole may be located a distance from a proximal end of the femoral nail 61-64% of a total length of the femoral nail, and the first axis of the dynamic screw hole may be located a distance from the proximal end of the femoral nail 71-74% of the total length of the femoral nail. Inserting the femoral nail into the intramedullary canal of the femur may include inserting the femoral nail across a fracture line extending from the greater trochanter to the lesser trochanter. The distal portion of the femoral nail may be canted relative to the intermediate straight portion by an angle $\Theta$. The angle $\Theta$ may be about 2 to 4 degrees.

In accordance with another aspect, the present disclosure relates to a femoral nail having a proximal portion, a distal portion remote from the proximal portion, and an intermediate portion. The proximal portion may be configured to engage a driving tool for driving the femoral nail into a femur. The intermediate portion may extend from and between the proximal portion and the distal portion, and the intermediate portion may have a circular screw hole and an elongated screw hole extending therethrough. The circular screw hole may have a central axis, and the elongated screw hole may have a first axis and a second axis that are separated by a distance. The central axis of the circular screw hole may be located a distance from a proximal end of the femoral nail that is 61-64% of a total length of the femoral nail, and the first axis of the elongated screw hole may be located a distance from the proximal end of the femoral nail that is 70-73% of the total length of the femoral nail. In such instances, the proximal portion may be straight along its entire length. The intermediate portion may include first and second curved segments and first and second straight segments. The first curved segment may define a proximal extent of the intermediate portion and the second straight segment may define a distal extent of the intermediate portion. The second curved segment may be disposed between the first and second straight segments and may have a radius of curvature in a first plane. The straight segment may have the circular screw hole and the elongated screw hole extending therethrough.

In such instances, the distal portion may be angled relative to the second straight segment of the intermediate portion by an angle $\Theta$, and the angle $\Theta$ may be 2 to 3 degrees. The distal portion may include a distal curved segment and a distal straight segment. The radius of curvature of the distal curved segment may be 120 mm. The femoral nail may have a total length of 240 mm. The distal portion may include a distal curved segment and a distal straight segment. The distal curved segment may be interfacing with the second straight segment of the intermediate portion and may extend distally therefrom. Additionally, the distal straight segment may extend from the distal curved segment to a distal tip of the femoral nail. The distal portion may interface with the second straight segment of the intermediate portion and may extend distally therefrom to a distal tip of the femoral nail. The distal portion may be curved along its entire length. The first curved segment of the intermediate portion may be curved in first, second, and third planes. The second curved segment may be curved in the first plane and only in the first plane. The distal curved segment may be curved in the same plane as that of the second curved segment. The femoral nail may be cannulated throughout its entire length. The proximal portion may include a transverse bore hole configured to receive a lag screw for insertion into a femoral neck of a femur.

In accordance with another aspect, the present disclosure relates to a femoral nail having a proximal portion, a distal portion remote from the proximal portion, and an intermediate portion. The proximal portion may be configured to engage a driving tool for driving the femoral nail into a femur and may define a proximal end of the femoral nail. The distal portion, remote from the proximal portion, may define a distal end of the femoral nail. The intermediate portion, extending from and between the proximal portion and the distal portion, may have a curved segment and a straight segment extending from the curved segment. The straight segment may have a proximal extent, a distal extent, and a circular screw hole and an elongated screw hole extending therethrough such that the proximal extent and the distal extent of the straight segment are respectively 57-60% and 80-83% of a total length of the femoral nail from the proximal end thereof. In such instances, the total length may be 240 mm. The proximal portion may be straight along its entire length. The distal portion may be angled relative to the straight segment of the intermediate portion by 2 to 3 degrees. The proximal extent of the curved segment may be 38-41% of the total length of the femoral nail from the proximal end of thereof and a distal extent of the curved segment may be the proximal extent of the straight segment.

In accordance with another aspect, the present disclosure relates to a bone repair system having a femoral nail, a targeting arm, and an aiming device. The femoral nail may include a proximal portion configured to engage a driving tool for driving the femoral nail into a femur, a distal portion remote from the proximal portion, and an intermediate portion extending from and between the proximal portion and the distal portion. The targeting arm may be adapted to attach to the proximal portion of the femoral nail. The aiming device may have a flange that may define a guide opening. The aiming device may be adapted to attach to an end of the targeting arm such that the guide opening is aligned with a screw hole in the femoral nail.

The aiming device may have a sleeve, a locking drive member, and a toggle locking member. The locking drive member may be adapted to secure the aiming device to targeting arm. The toggle locking member may be adapted to secure a cannula placed within the guide opening. The intermediate portion of the femoral nail may have a first straight segment and a second straight segment separated by a curved segment, and the second straight segment may define the screw hole. The screw hole may be an elongated opening. The guide opening may have a profile of two intersecting circles. The toggle locking member may be in communication with the guide opening. The locking drive member may be at least partially disposed within the flange. The sleeve may define a channel having a first opening and a second opening. The channel may be configured to receive the targeting arm at the first opening and/or the second opening. The femoral nail may have a plurality of screw holes. The aiming device may have a plurality of guide openings, and each of the plurality of guide openings may be configured to align with one of the plurality of screw holes without adjustments to obtain proper alignment. The spacing between each pair of the plurality of guide openings may be equal to a spacing between each pair of the plurality of screw holes. The aiming device and the targeting arm both may include markings that indicate proper positioning of the aiming device with respect to the targeting arm. The bone repair system may further include a cannula, a scalpel, and a drill bit. The cannula may be open at both ends and may be configured to be received by the guide opening of the aiming device. The scalpel may be configured to be inserted through the cannula. The drill bit may be configured to be inserted through the cannula.

In accordance with yet another aspect, the present invention relates to a process of repairing a proximal femoral fracture. The process may include a femoral nail inserted into an intramedullary canal of a femur from a proximal end thereof such that a distal end of the femoral nail is positioned proximal of a femoral isthmus of the femur. The femoral nail may have a proximal portion, a distal portion, and an intermediate portion. The proximal portion may have a transverse bore hole, and the intermediate portion may have a first screw hole and a second screw hole extending therethrough. Then a targeting arm may be attached to a proximal end a femoral nail. Once the targeting arm is attached, a lag screw may be inserted through the transverse bore hole across at least one fracture line in the proximal femur such that a distal end of the lag screw is disposed at least partially within a femoral head of the femur. Next, an aiming device having a first guide opening and a toggle locking member may be attached to the targeting arm such that the first guide opening is aligned with the first screw hole. Once this is aligned, a cannula may be secured within the first guide opening by locking the toggle locking member. Then a bone screw may be aligned with the first screw hole by placing the bone screw within the cannula. At this point, the bone screw may be advanced through the cannula to the first screw hole and into the bone.

In such instances, the attachment of the aiming device to the targeting arm may include positioning the aiming device on the targeting arm until tactile feedback is provided to the user by the aiming device. The repair process may further include a driving member of the aiming device being locked after the tactile feedback has been provided. After attachment the aiming device to the targeting arm, the cannula may be inserted through the first guide opening and through an incision until the cannula contacts the femur. The cannula may be released from within the first guide opening by pressing the toggle locking member. The advancement of the bone screw may be done by pushing the bone screw through the cannula with a drill bit. Additionally, another bone screw may be aligned with and inserted through a second guide opening and into a second screw hole.

BRIEF DESCRIPTION OF THE DRAWINGS

The features, aspects, and advantages of the present invention will become better understood with regard to the following description, appended claims, and accompanying drawings in which:

FIG. 8A is a side view of a modular targeting device according to an embodiment of the present disclosure.

FIG. 8B is a front view of the modular targeting device of FIG. 8A.

FIG. 8C is a cross-sectional view of the modular targeting device of FIG. 8A taken along line C-C of FIG. 8B.

FIGS. 9A and 9B illustrate a method of implanting the femoral nail of FIG. 3 into a femur.

FIG. 9C illustrates a first bone screw configuration of the femoral nail of FIG. 3 that can be achieved after implantation.

FIG. 9D illustrates a second bone screw configuration of the femoral nail of FIG. 3 that can be achieved after implantation.

DETAILED DESCRIPTION

Figures 1, 2A, 2B:
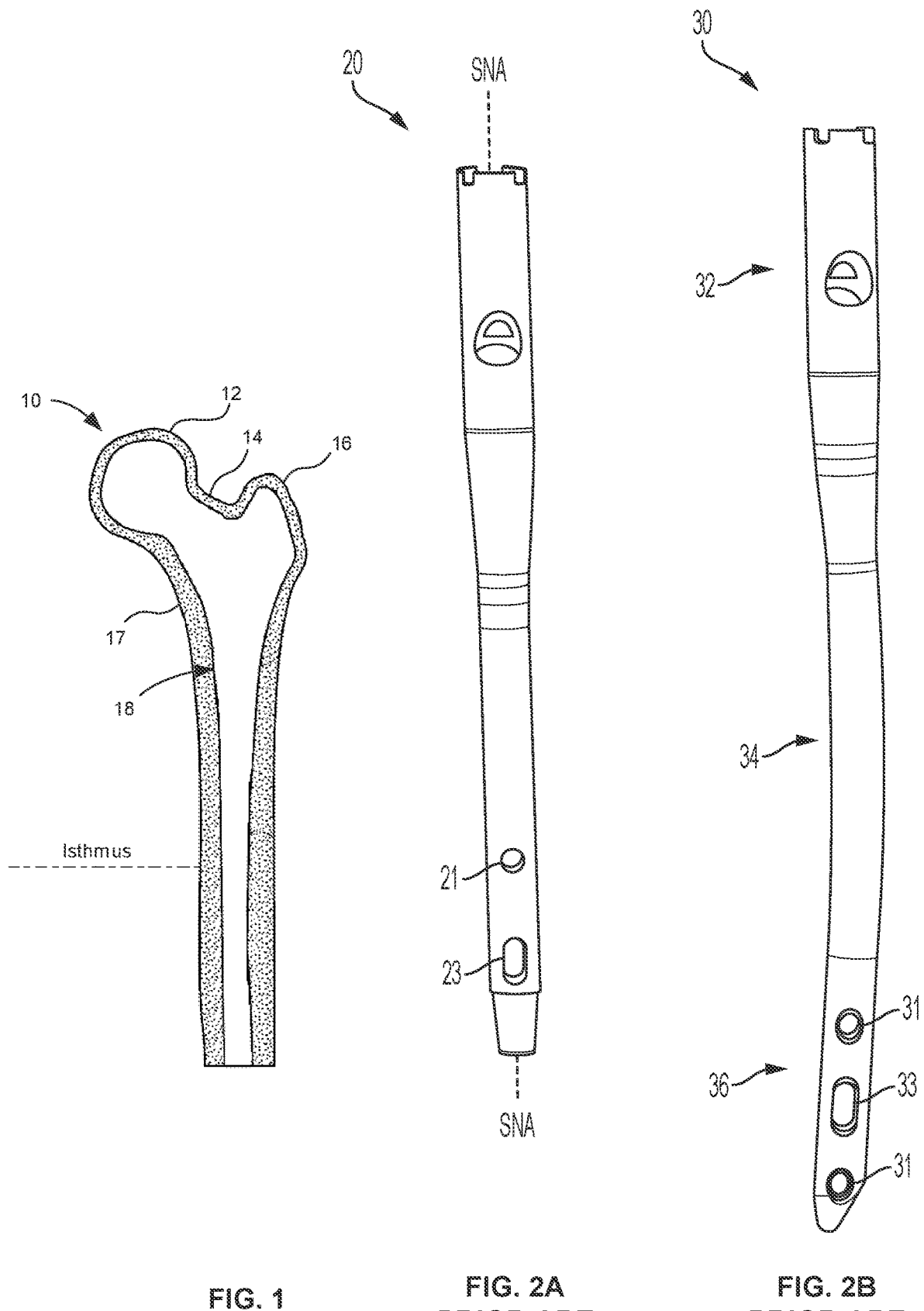
FIG. 1 is a partial schematic cross-sectional view of a femur.
FIG. 2A is a perspective view of a short femoral nail according to the prior art.
FIG. 2B is a perspective view of a long femoral nail according to the prior art.

As used herein, the term "proximal," when used in connection with a surgical tool or device, or components of a device, refers to the end of the device closer to the user of the device when the device is being used as intended. On the other hand, the term "distal," when used in connection with a surgical tool or device, or components of a device, refers to the end of the device farther away from the user when the device is being used as intended. However, when these terms are used in connection with the human body, "proximal" means closer to the heart, and the term "distal" means further from the heart. As used herein, the terms "substantially," "generally," "approximately," and "about" are intended to mean that slight deviations from absolute are included within the scope of the term so modified, such as deviations of up to 10% greater or lesser than absolute.

FIGS. 3-7 depict a femoral nail 100 according to an embodiment of the present disclosure. Femoral nail 100 is an intermediate intramedullary femoral nail. In this regard, it has an intermediate length between that of commonly understood short and long nails and is universal to a designated patient population irrespective of the length of a particular patient's femur within that population, as described in more detail below. Femoral nail 100, as depicted, is configured for a left leg femur. However, it should be understood that the features of femoral nail 100 can be configured for a right leg femur such that it would include the same features described herein but as a mirror image. Femoral nail 100 is used, together with other devices, such as bone fasteners, as will be described herein, to achieve functionally stable osteosyntheses and stabilization of bone until fusion occurs.

Femoral nail 100 generally includes a proximal portion 110, an intermediate portion 120, and a distal portion 130. Proximal portion 110 extends straight along a central axis CA of nail 100. Proximal portion 110 has a cylindrical segment 110a that extends from a proximal end of nail 100, and a conical segment 110b that extends from cylindrical segment 110a to the intermediate portion 120. Conical segment 110b tapers in a distal direction such that the diameter of nail 100 reduces to a smaller diameter from that of cylindrical segment 110a.

Figures 3, 4, 5:
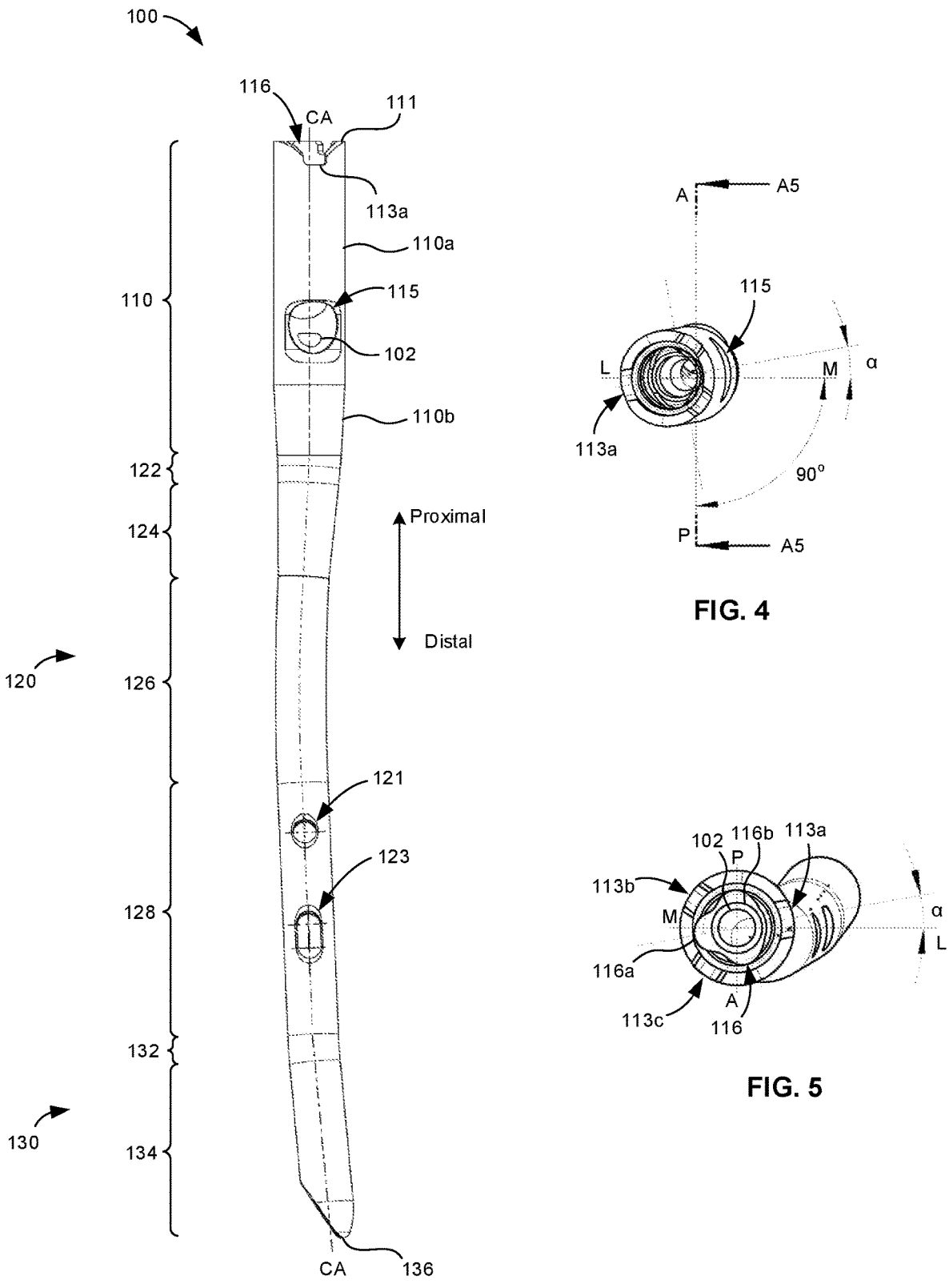
FIG. 3 is a medial side view of a femoral nail according to an embodiment of the present disclosure.
FIG. 4 is a top view of the femoral nail of FIG. 3.
FIG. 5 is another top view of the femoral nail of FIG. 3.

Proximal portion 110 includes an axial bore or proximal chamber 116 which extends into nail 100 from the proximal end thereof. A transverse or lateral bore 115 extends through proximal portion 110 transverse to central axis CA at an oblique angle relative thereto and intersects axial bore 116. Transverse bore 115 is configured to receive a bone fastener and, in particular, a lag screw, such as the lag screw 140 shown in FIG. 9B. As shown in FIGS. 4 and 5, axial bore 116 includes a first aperture 116a and a second aperture 116b that define the bore 116 at opposing ends thereof. First aperture 116a is located closer to a proximal end 111 of nail 100 than second aperture 116b and is a tri-lobed aperture in that it has three radially outwardly extending lobes arranged about central axis CA. Second aperture 116b is circular and is located at a distal end of axial bore 116. Axial bore 116 in this respect is configured to receive a set screw which is moveable therein in a manner to engage and secure lag screw 140. An exemplary set screw that is configured to be received within axial bore can be found in International Pub. No. WO 2021/176274, which is hereby incorporated by reference herein in its entirety. Other axial bore and set screw configurations that may be included in femoral nail 100 can be found in EP Patent No. 0,257,118; U.S. Pat. Nos. 5,176,681; 5,454,813 and 11,253,298; International Pub. No. WO 2021/176272, all of which are hereby incorporated by reference herein their entireties.

Proximal portion 110 also includes a plurality of alignment notches that extend into a sidewall of nail from a proximal end of nail. Alignment notches 113 are arranged about central axis CA in the manner depicted in FIGS. 4 and 5. In particular, nail 100 has a first alignment notch 113a, a second alignment notch 113b, and a third alignment notch 113c. Such notches 113 may be configured to engage corresponding features of an insertion tool and/or targeting tool, such as targeting arm 70 of FIG. 9A, and may assist the operator to properly orient nail 100 so that its geometric features are properly aligned with those of the femur 10. As shown in FIG. 4, a center axis of first alignment notch 113a is coplanar with a center axis of transverse bore 115. Such plane and corresponding axes are oriented relative to a lateral-medial plane by an anteversion angle α which generally corresponds to an anteversion angle of a patient's femur 10. Angle α may be 10 degrees, for example. Thus, when nail 100 is implanted in femur 10, transverse bore 115 is preferably aligned with a femoral neck 14 of femur 10 while curvatures of nail 100 conform to an anterior bow of femur 10 in an anteroposterior plane.

Intermediate portion 120 extends distally from proximal portion 110 and generally includes a first curved or bent segment 122, second curved or bent segment 126, first straight segment 124, and second straight segment 128. First curved segment 122 interfaces with conical segment 110b of proximal portion 110 and is curved or bent in three planes in a manner that helps prevent impingement of nail 100 with an anterior cortex of femur 10. First straight segment 124 interfaces with first curved segment 122 and extends therefrom such that it is straight along its length and along central axis CA. The geometries of first curved segment 122 and first straight segment 124, including their relationship with proximal portion 110, are described in more detail in U.S. Pat. No. 11,013,540, which is hereby incorporated by reference herein in its entirety. However, it is noted here that first curved segment 122 has a first curvature that is curved or bent in an anteroposterior plane (first plane), a second curvature that is curved or bent in a mediolateral plane (second plane), and a third curvature that is curved or bent in a resultant/intermediate plane (third plane). Each of these planes intersect at a common origin which may be a cranial-caudal/proximal-distal axis. In other words, the first curved segment 122 is defined by a third bend of a non-zero radius of curvature in the third plane such that the third bend is a resultant of a first bend within the first plane and a second bend within the second plane. The first and second planes intersect at an oblique angle relative to each other such that a reference plane orthogonal to the first plane extends between the second and third planes. Moreover, the magnitude of the angle of the third curvature in the third plane is a resultant of the magnitudes of the bend angles of the first and second curvatures in their respective first and second planes. Therefore, the third bend angle may be larger than the first and second bend angles.

Figures 6, 7:
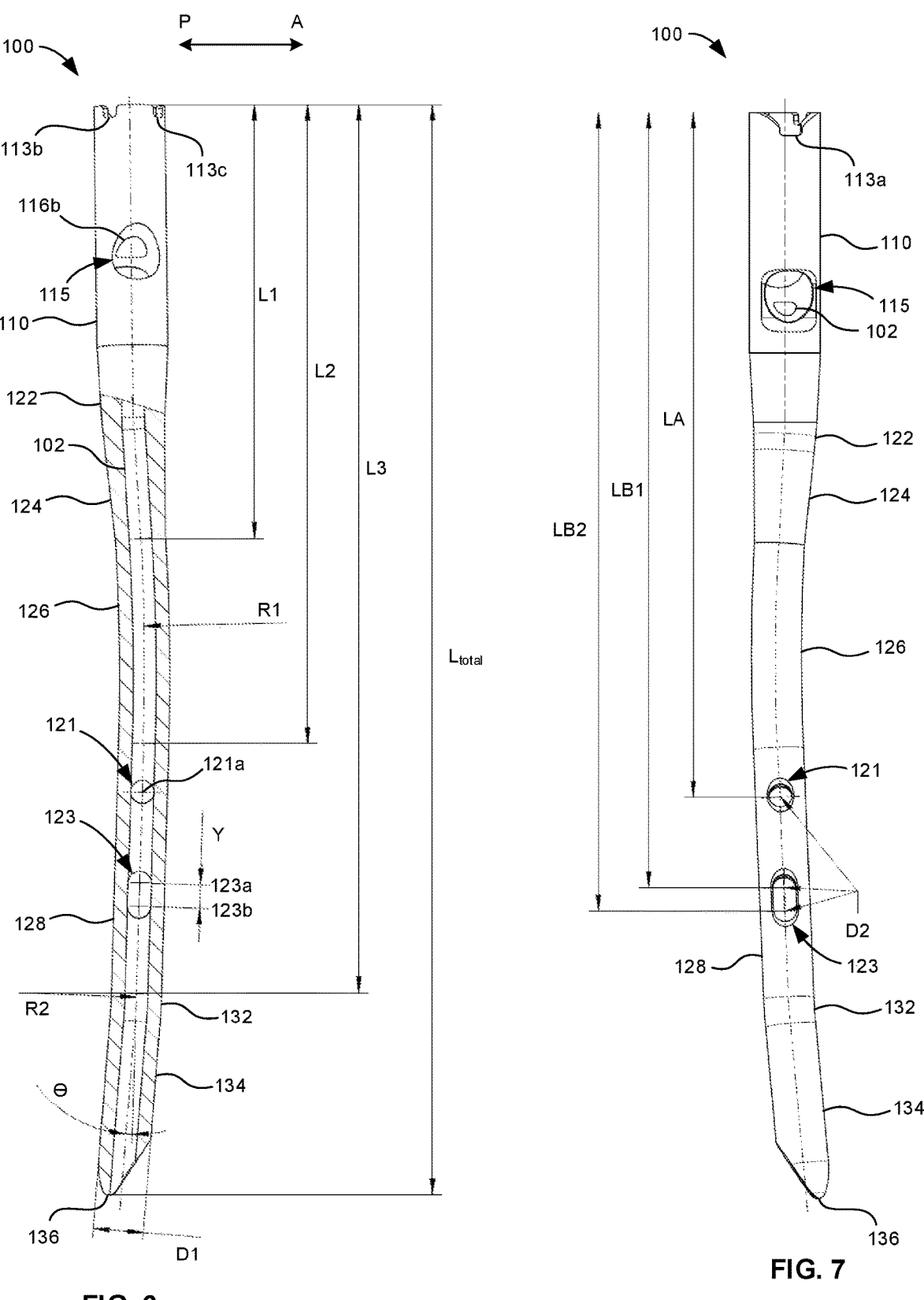
FIG. 6 is a partial cross-sectional view of the femoral nail taken along line A5 of FIG. 4.
FIG. 7 is a lateral side view of the femoral nail of FIG. 3.

Second curved segment 126 extends distally from first straight segment 124 and is curved or bent in the antero-posterior plane and only the anteroposterior plane so that it defines a radius of curvature R1, as best shown in FIG. 6 which depicts the anteroposterior plane. Radius R1 is 350 mm to 650 mm, for example, but is preferably 500 mm.

Second straight segment 128 extends distally from second curved segment 126 and includes a plurality of screw holes 121, 123. In particular, second curved segment 126 includes a first screw hole 121 and a second screw hole 123. In the embodiment depicted, first screw hole 121 is a static screw hole while second screw hole 123 is an elongate screw hole or dynamic compression screw hole. In this regard, first screw hole 121 is a circular screw hole that has a single hole axis 121*a* and hole radius. Second screw hole 123, on the other hand, is an elongate screw hole that has two axes 123*a-b* separated by a distance Y, as shown in FIG. 6. A hole radius extending about each of such axes 123*a-b* forms at least a portion of elongate screw hole. The positioning of screw holes 121, 123 on straight segment 128 facilitates ease of screw hole targeting when nail is implanted within femur as compared to if screw holes 121, 123 were located on a curved segment 126 or distal portion 130, as described in more detail below.

Distal portion 130 extends distally from intermediate portion 120 such that intermediate portion 120 extends between proximal portion 110 and distal portion 130. In the embodiment depicted, distal portion 130 includes a distal curved or bent segment 132 and distal straight segment 134. Distal curved segment 132 is curved or bent such that it has the effect of orientating distal straight segment 134 relative to second straight segment 128 of intermediate portion at an angle Θ. Such bend or canted angle Θ can be about 2 degrees to about 4 degrees, for example, but is preferably 2.9 degrees. In other words, straight segment 134 defines an axis that is angled relative to an axis of distal portion 130 by the angle Θ. As shown, distal curved segment 132 has a radius of curvature R2 in the anteroposterior plane, and only in the anteroposterior plane. In this regard, R1 and R2 are coplanar. In other words, second curved segment 126 of intermediate portion 120 and distal curved segment 132 of distal portion 130 are curved or bent in the same plane. R2 may be 120 mm, for example.

An axial channel 102 extends through proximal portion 110, intermediate portion 120, and distal portion 130. As shown in FIG. 3, axial channel 102 intersects transverse bore 115 across transverse bore 115 from second aperture 116*b* of proximal chamber 116. Thus, nail 100 is cannulated along its entire length so that nail 100 can be guided along a wire, such as a K-wire, into an intramedullary canal 18 of femur 10 during implantation thereof.

As previously mentioned, nail 100 is an intermediate length nail. In this regard, nail 100 has a total length $L_{total}$ that is generally between what is commonly understood as a short nail and a long nail. More specifically, the total length $L_{total}$ of intermediate nail 100 is such that it is the longest length possible without breaching the isthmus of a standard deviation of femurs within a designated patient population. In other words, $L_{total}$ may be equal to or less than a length between an insertion location and an opening to the femoral isthmus of 68%, 95%, or 99.7% (i.e., first, second, or third standard deviations) of a designated population of patient femurs. For example, $L_{total}$ of nail 100 depicted in the figures is 240 mm which will not breach the isthmus of a second standard deviation (i.e., 95%) of a total possible patient population (i.e., broadest possible patient population). As such, intermediate nail 100 has a universal total length $L_{total}$ of 240 mm. However, the designated patient population may be more specific and selected based on certain characteristics of a particular patient. Thus, $L_{total}$ is generally dependent on the designated population.

$L_{total}$ can be determined through a population analysis of bones maintained in a bone database such as the Stryker® Orthopaedics Modeling and Analytics (SOMA) system by Stryker® Corporation, for example. In this regard, a diverse set of femurs may be selected from the database so that it is representative of the entire patient population, as mentioned in the example above, or representative of a specific subset of the entire patient population which may be based on certain characteristics, such as, weight, height, age, sex, ethnic group, and the like. For example, the designated patient population may be "female." Therefore, the analysis to determine $L_{total}$ for the female population includes selecting bones from the bone database that are representative of the entire female population within a particular geographic region or worldwide. Such bones are then analyzed to determine the distance of the proximal opening of the femoral isthmus from a proximal entry point of the femur for each bone. Such entry point may be at the greater trochanter 16, for example. These measured distances are then statistically analyzed to determine a mean distance and first, second, and third standard deviations therefrom. The total length $L_{total}$ of nail 100 may then be correlated to the first, second, or third standard deviations, as desired. Although the length of the intermediate nail 100 may be consistent for a selected population, intermediate nail 100 may have different diameters D1 for that population. Such diameters may be about 9 mm to 13 mm.

The lengths of certain features of nail 100 may similarly be determined by reference to specific anatomical features of a femur and optimized based on the bone database in a similar manner mentioned above to help ensure a conformal fit for most patients. As shown in FIGS. 6 and 7, nail includes lengths L1, L2, L3, LA, LB1, and LB2 which each define one or more feature of nail 100. Specifically, L1 and L2 respectively define proximal and distal extents of second curved segment 126 of intermediate portion 120 as measured proximal end 111 of nail 100. L2 and L3 also respectively define proximal and distal extents of second straight segment 128 of intermediate portion 120 as measured from proximal end 111. Additionally, L3 defines a proximal extent of distal segment 130 and distal curved segment 132 as measured from proximal end 111. As an example, L1 may be 95 mm, L2 may be 140 mm, and L3 may be 195 mm. However, L1 may be about 38-41% of $L_{total}$, L2 may be 57-60% of $L_{total}$ and L3 may be 80-83% of $L_{total}$.

Lengths LA, LB1, and LB2 define locations of screw holes. In this regard, LA is the distance of center axis 121*a* of first hole from proximal end, LB1 is the distance of first axis 123*a* of hole 123 from proximal end, and LB2 is the distance of second axis 123$b$ from proximal end. As an example, LA may be 150.5 mm, LB1 may be 170.45 mm, and LB2 may be 175.58 mm. However, LA may be 61-64% of $L_{total}$, LB1 may be 70-73% of $L_{total}$ and LB2 may be 71-74% of $L_{total}$.

As mentioned above, the location of screw holes 121 and 123 facilitates simpler screw targeting as compared to a long nail with screw holes positioned more distal along the length of the nail, such as with long nail 30 of FIG. 2B. FIGS. 8A-8C depict a modular aiming device 40 that may be used to target screw holes 121 and 123. Aiming device 40 generally includes a sleeve 42, a flange 44, a locking drive member 50, and a toggle locking member 60.

Sleeve or connection member 42 is generally cylindrical and includes a channel or axial opening 45 extending therethrough that is configured to receive a targeting arm, such as arm 70 of FIG. 9A. Sleeve 42 is such that it can receive targeting arm 70 from either end of channel 45 so that aiming device 40 can be used for both left leg femurs and right leg femurs.

Flange or guide body 44 is coupled to a side of sleeve 42 between opposing ends thereof and extends radially outwardly from sleeve 42. Flange 44 includes a first guide opening 41 and a second guide opening 43 each extending through flange 44. First guide opening 41 has a generally circular profile, while second guide opening 43 has a profile of two intersecting circles. In this regard, first guide opening 41 is adapted to guide instruments toward first screw hole 121, while second guide opening 43 is adapted to guide instruments toward second screw hole 123. As such, center axes of each guide opening are offset from each other the same distances as axes 121$a$ and 123$a$-$b$ of screw holes. In this manner, when aiming device 40 is properly attached to targeting arm 70, first guide opening 41 is aligned with first screw hole 121, and second guide opening 43 is aligned with second screw hole 123.

Flange 44 also includes a chamber 48 which intersects first and second guide openings 41, 43. Toggle locking member 60 is disposed in such chamber 48 and is configured to toggle between at least two positions such that in one position, first and second openings 41, 43 are unobstructed, and in another position, toggle locking member 60 partially obstructs openings 41, 43. This allows for a device, such as cannula 80 of FIG. 9A, to be secured within a respective opening 41, 43 by toggle locking member 60 when in the second position.

Flange 44 also houses a locking drive member 50 which generally includes a knob 51, threaded shaft 52, spring 54, and plunger 55. Plunger 55 extends from flange 44 and into channel 45 of sleeve 42 and is moveable in a direction transverse to channel 45. Threaded shaft 52 is threadedly engaged to flange 44. A distal end 43 of threaded shaft 52 is separate from and moveable relative to plunger 55. Spring 54 overlaps the gap between distal end 53 and plunger 55. When knob 51 is rotated in a first direction, spring 54 compresses and distal end 53 bears against plunger 55 causing plunger 55 to extend into channel 45 and to secure sleeve 42 to a targeting arm 70 received therein. When knob 51 is rotated in a second direction, the gap between distal end 43 and plunger 55 is reformed which relieves pressure from plunger 55 so that sleeve 42 can be removed from targeting arm 70. This arrangement allows threaded shaft 52 to be rotated relative to plunger 55 so that plunger 55 is only moved translationally which helps prevent wear to targeting arm.

Upon insertion of nail 100, as shown in FIGS. 9A and 9B, nail 100 generally follows the natural curvature of femur 10 proximal of the femoral isthmus. After insertion, a targeting arm 70 is connected to proximal end 111 of nail 100. Alignment notches 113$a$-$c$ help set the rotational orientation of targeting arm 70. Sleeve 42 of modular aiming device 40 may then be slid over a distal end of targeting arm 70 and secured thereto via locking drive member 50. In some embodiments, aiming device 40 may provide tactile feedback when it is properly oriented with respect to targeting arm 70, e.g., but not limited to, a clicking sound or vibration, to notify the user that the aiming device has been correctly positioned before securing with locking drive member 50. Markings and/or other features may help set the rotational orientation and depth of aiming device 40 on targeting arm 70. A cannula 80 can then be inserted into a guide opening 41, 43. In some embodiments, after cannula 80 has been properly positioned against the skin, a scalpel instrument may be inserted into the cannula to make an incision through which the cannula can be passed until contact is made with bone 10. A drill bit 90 may then be guided by cannula 80 to drill through bone 10 and into one of screw holes 121, 123. Because second guide opening 43 is formed of two circular shapes, cannula 80 can be guided by either shape depending on a desired locking screw arrangement, as described below. Also, the locations of screw holes 121, 123 along second straight segment 128 of intermediate portion 120 proximal of distal portion 130 allows this screw hole targeting procedure to be performed without the aid of fluoroscopy and with minimal adjustments necessary to achieve proper alignment. Additionally, the conformal curvatures of nail 100 and its extended length relative to that of short nails helps provide additional stability compared to short nails.

Thereafter, a lag screw 140 may be inserted through lateral bore 115 to secure a variety of fractures involving the greater trochanter 16, femoral head 12, and/or femoral neck 14. For example, as shown in FIG. 9B, femur 10 may have a pertrochanteric fracture with at least one fracture line 19 extending between the greater trochanter 18 and lesser trochanter 17. In such a fracture pattern, nail 100 is inserted across fracture line 19. Thereafter, lag screw 140 is inserted through lateral bore 115 across fracture line 19 such that at least a portion of lag screw 140 is positioned within femoral head 12.

Figure 9E:
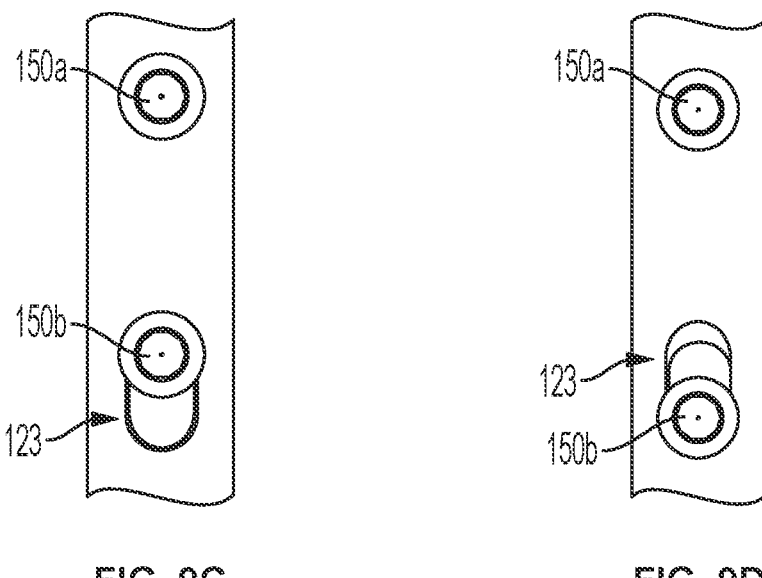
FIG. 9E illustrates a third bone screw configuration of the femoral nail of FIG. 3 that can be achieved after implantation.
Figure 9E:
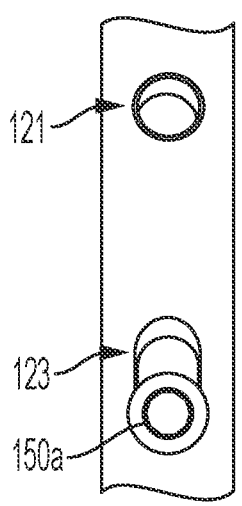

Additionally, other bone fasteners, such as bone screws 150, are inserted through one or both screw holes 121 and 123, as shown in FIGS. 9B-9E. In particular, femoral nail 100 may have a first screw configuration or static locking configuration, as shown in FIG. 9C, in which a first bone screw 150$a$ is inserted through hole 121, and a second bone screw 150$b$ is inserted through a proximal end of screw hole 123 generally coaxial with center axis 123$a$. In such configuration, femoral nail 100 is statically secured to bone 10. In a second screw configuration or secondary dynamization configuration, as shown in FIGS. 9B and 9D, first bone screw 150$a$ is inserted through hole 121, and second bone screw 150$b$ is inserted through a distal end of screw hole 123 generally coaxial with second axis 123$b$. In such configuration, femoral nail 100 is initially statically secured to bone 10. However, removal of first bone screw 150$a$ creates a third configuration or dynamic locking configuration, as shown in FIG. 9E, which allows for dynamization. In such dynamic locking configuration, first or second bone screw 150$a$-$b$ is positioned through the distal end of screw hole 123 thereby allowing nail 100 and bone 10 to move relative to each other.

The various bone screw configurations mentioned above including the dynamization feature, is facilitated by screw holes 121 and 123 being located within the second straight segment 128 of intermediate portion 130. In other words, the straight geometry of straight segment 128 facilitates ease of targeting screw holes 121 and 123 and dynamic movement of nail 100 when using the dynamic locking configuration. It is also noted that second straight segment 128 is positioned between distal portion 130 and second curved segment 126. This arrangement provides a conformal geometry at both ends of straight segment 128.

Figure 10:
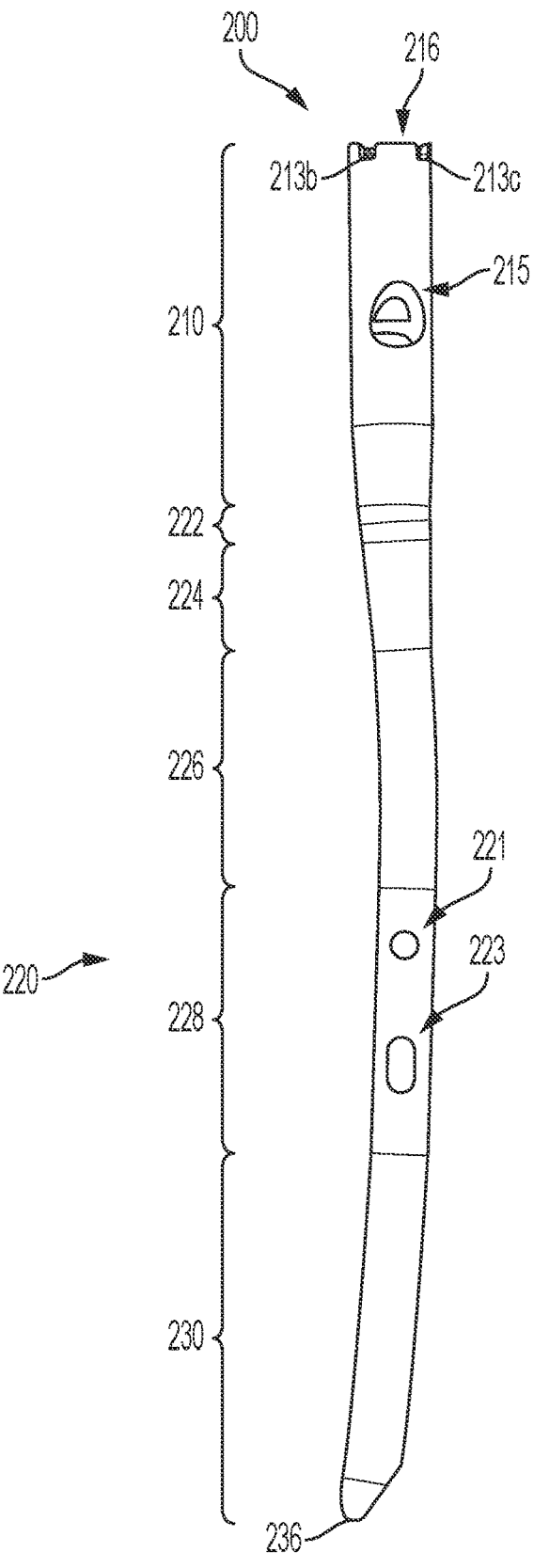
FIG. 10 is a medial view of a femoral nail according to another embodiment of the present disclosure.

FIG. 10 depicts a femoral nail 200 according to another embodiment of the present disclosure. For ease of review, like elements are accorded like reference numerals to that of femoral nail 100 but within the 200-series of numbers. For instance, femoral nail 200 includes a proximal portion 210 and intermediate portion 220 which are like proximal portion 110 and intermediate portion 120 of nail 100. However, nail 200 differs in that distal portion 230 of femoral nail 200 is curved along its entire length from an interface with second straight segment 228 of intermediate portion 220 to distal tip 236. In this regard, distal portion 230 has a radius of curvature R2' in the anteroposterior plane which forms a resultant bend angle or canted angle of the distal portion 230 to relative to straight segment 228 of 2 to 4 degrees, but preferably three degrees.

Although the nails 100, 200 shown and described herein are configured to receive a lag screw for proximal femoral fractures, other bone fastener configurations within proximal portion of nail 100 are contemplated to address other fracture profiles. An example of such bone fastener configuration can be found in the heretofore incorporated U.S. Pat. No. 11,013,540.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A femoral nail, comprising:
a proximal portion configured to engage a driving tool for driving the femoral nail into a femur;
a distal portion remote from the proximal portion; and
an intermediate portion extending from and between the proximal portion and the distal portion, the intermediate portion having a circular screw hole and an elongated screw hole extending therethrough, the circular screw hole having a central axis, and the elongated screw hole having a first axis and a second axis that are separated by a distance,
wherein the central axis of the circular screw hole is located a distance from a proximal end of the femoral nail that is 61-64% of a total length of the femoral nail, and the first axis of the elongated screw hole is located a distance from the proximal end of the femoral nail that is 70-73% of the total length of the femoral nail.

2. The femoral nail of claim 1, wherein the proximal portion is straight along its entire length.

3. A femoral nail, comprising:
a proximal portion configured to engage a driving tool for driving the femoral nail into a femur;
a distal portion remote from the proximal portion; and
an intermediate portion extending from and between the proximal portion and the distal portion, the intermediate portion having a circular screw hole and an elongated screw hole extending therethrough, the circular screw hole having a central axis, and the elongated screw hole having a first axis and a second axis that are separated by a distance,
wherein the central axis of the circular screw hole is located a distance from a proximal end of the femoral nail that is 61-64% of a total length of the femoral nail, and the first axis of the elongated screw hole is located a distance from the proximal end of the femoral nail that is 70-73% of the total length of the femoral nail, and
wherein the intermediate portion includes first and second curved segments and first and second straight segments, the first curved segment defining a proximal extent of the intermediate portion and the second straight segment defining a distal extent of the intermediate portion, the second curved segment being disposed between the first and second straight segments and having a radius of curvature in a first plane, the straight segment having the circular screw hole and the elongated screw hole extending therethrough.

4. The femoral nail of claim 3, wherein the distal portion is angled relative to the second straight segment of the intermediate portion by an angle Θ.

5. The femoral nail of claim 4, wherein the angle Θ is 2 to 3 degrees.

6. The femoral nail of claim 4, wherein the distal portion includes a distal curved segment and a distal straight segment.

7. The femoral nail of claim 6, wherein the radius of curvature of the distal curved segment is 120 mm.

8. The femoral nail of claim 1, wherein the femoral nail has a total length of 240 mm.

9. The femoral nail of claim 3, wherein the distal portion includes a distal curved segment and a distal straight segment, the distal curved segment interfacing with the second straight segment of the intermediate portion and extending distally therefrom, the distal straight segment extending from the distal curved segment to a distal tip of the femoral nail.

10. The femoral nail of claim 3, wherein the distal portion interfaces with the second straight segment of the intermediate portion and extends distally therefrom to a distal tip of the femoral nail, the distal portion being curved along its entire length.

11. The femoral nail of claim 3, wherein the first curved segment of the intermediate portion is curved in first, second, and third planes.

12. The femoral nail of claim 10, wherein the second curved segment is curved in the first plane and only in the first plane.

13. The femoral nail of claim 11, wherein the distal curved segment is curved in the same plane as that of the second curved segment.

14. The femoral nail of claim 1, wherein the femoral nail is cannulated throughout its entire length.

15. The femoral nail of claim 13, wherein the proximal portion includes a transverse bore hole configured to receive a lag screw for insertion into a femoral neck of a femur.

16. A femoral nail, comprising:
a proximal portion configured to engage a driving tool for driving the femoral nail into a femur and defining a proximal end of the femoral nail;
a distal portion remote from the proximal portion and defining a distal end of the femoral nail; and
an intermediate portion extending from and between the proximal portion and the distal portion, the intermediate portion having a curved segment and a straight segment extending from the curved segment, the straight segment having a proximal extent, a distal extent, and a circular screw hole and an elongated screw hole extending therethrough, wherein the proximal extent and the distal extent of the straight segment are respectively 57-60% and 80-83% of a total length of the femoral nail from the proximal end thereof.

17. The femoral nail of claim 16, wherein the total length is 240 mm.

18. The femoral nail of claim 16, wherein the proximal portion is straight along its entire length.

19. The femoral nail of claim 16, wherein the distal portion is angled relative to the straight segment of the intermediate portion by 2 to 3 degrees.

20. The femoral nail of claim 16, wherein a proximal extent of the curved segment is 38-41% of the total length of the femoral nail from the proximal end of thereof and a distal extent of the curved segment is the proximal extent of the straight segment.

* * * * *